US008160854B2

(12) United States Patent
Fujisaki et al.

(10) Patent No.: US 8,160,854 B2
(45) Date of Patent: Apr. 17, 2012

(54) METHOD OF MANAGING AND DISPLAYING GENE EXPRESSION DATA

(75) Inventors: Ayako Fujisaki, Tokyo (JP); Noriyuki Yamamoto, Tokyo (JP); Atsushi Mori, Tokyo (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 1188 days.

(21) Appl. No.: 10/929,792

(22) Filed: Aug. 31, 2004

(65) Prior Publication Data

US 2005/0089900 A1    Apr. 28, 2005

(30) Foreign Application Priority Data

Oct. 27, 2003  (JP) ................................. 2003-366003

(51) Int. Cl.
*G06G 7/48* (2006.01)
*G01N 33/48* (2006.01)

(52) U.S. Cl. ........................................... 703/11; 702/19
(58) Field of Classification Search .................. None
See application file for complete search history.

(56) References Cited

OTHER PUBLICATIONS

Alon et al. "Broad patters of gene expression revealed by clustering analysis of tumor and normal colon tissues probed by oligonucleotide arrays" Proc. Natle. Acad. Sci., USA (1999) vol. 96, pp. 6745-6750.*
Chris Stolte et al., Polaris: A System for Query, Analysis, and Visualization of Multidimensional Relational Databases:, IEEE Transactions on Visualization and Computer Graphics, vol. 8, No. 1, (Jan.-Mar. 2002), pp. 52-65.
Stephen G. Eick, "Visualizing Multi-Dimensional Data", Computer Graphics ACM USA, vol. 34, No. 1, (Feb. 2000), pp. 61-67.
Hao Wu et al., "MAANOVA: A Software Package for the Analysis of Spotted cDNA Microarray Experiments", Chapter of the Analysis of Gene Expression Data: Methods and Software Online, http://www.jax.org/staff/churchill/labsite/pubs/Wu-maanova.pdf>, (2002), pp. I-XLIX.
Lao H. Saal et al., "BioArray Software Environment (BASE): A Platform for Comprehensive Management and Analysis of Microarray Data", Genome Biology, vol. 3, No. 8, (Jul. 15, 2002), pp. 1-6.
Jason Comander et al., "Argus-A New Database System for Web-Based Analysis of Multiple Microarray Data Sets", Genome Research, vol. 11, No. 9, (Sep. 2001), pp. 1603-1610.
European Search Report dated Feb. 3, 2006.

* cited by examiner

*Primary Examiner* — Eric S Dejong
(74) *Attorney, Agent, or Firm* — Stites & Harbison, PLLC; Juan Carlos A. Marquez, Esq

(57) ABSTRACT

A method visually and clearly manages and displays a large amount of gene expression data obtained using a large number of DNA chips. The types of DNA chip are displayed in a leftmost column of a matrix, parameters such as times in a time series, treatment methods, types of samples, and the like are displayed in the top row, and expression value data corresponding to the respective cells are displayed as small matrices. Treatment methods or types of samples of Channel 1 and Channel 2 are displayed in the rows and columns of the small matrices. When a cell in a small matrix is clicked, a scatter diagram for corresponding expression value data is displayed.

9 Claims, 11 Drawing Sheets

FIG. 4

| Hybridization ID 400 | Repeated Experiment Unit 401 | Chip Type 402 | Parameter 403 | Ch1 Treatment Method 404 | Ch2 Treatment Method 405 | Ch1 Sample 406 | Ch2 Sample 407 | Block 408 | Spot 409 |
|---|---|---|---|---|---|---|---|---|---|
| 1 | 1 | Subset A | 2h | A1 | B1 | Mouse | Mouse | 48 | 225 |
| 2 | 1 | Subset A | 2h | A2 | B2 | Mouse | Mouse | 48 | 225 |
| 3 | 1 | Subset A | 2h | B1 | A2 | Mouse | Mouse | 48 | 225 |
| 4 | 1 | Subset A | 2h | B2 | A1 | Mouse | Mouse | 48 | 225 |
| ... | ... | ... | ... | ... | ... | ... | ... | ... | ... |
| N | X | Subset C | 10h | A1 | B2 | Mouse | Mouse | 44 | 225 |

FIG. 5

| Hybridization ID | Probe ID | Ch1 Intensity | Ch2 Intensity |
|---|---|---|---|
| 1 | Oligo001 | 751 | 664 |
| 1 | Oligo002 | 27 | 57 |
| 1 | Oligo003 | 836 | 741 |
| ... | ... | ... | ... |
| N | Oligo00M | 1022 | 569 |

| Probe ID | Description | Accession No1 | Accession No2 | Note1 | Note2 |
|---|---|---|---|---|---|
| Oligo001 | interferon | NM_002170 | 3445 | ... | ... |
| Oligo002 | activator | NM_004553 | 2219 | ... | ... |
| ... | ... | ... | ... | ... | ... |
| OligoM | GAPDH mRNA | NM_223425 | 7891 | ... | ... |

| File Name | Chip Type | Parameter | Ch1 Treatment Method | Ch2 Treatment Method | Ch1 Sample | Ch2 Sample |
|---|---|---|---|---|---|---|
| Aset.txt | | | | | | |
| Bset.txt | | | | | | |
| Cset.txt | | | | | | |
| Dset.txt | | | | | | |
| Eset.txt | | | | | | |
| Fset.txt | | | | | | |
| Gset.txt | | | | | | |
| Hset.txt | | | | | | |

Experiment Name 701 702 703 704 705 706 707

708 Select Repeated Experiment
709 Cancel Selection
711
712 FILL DOWN
713 Add Information
714 Delete 710 Processing Method for Repeated Experiment
o Calculation Method 1
o Calculation Method 2

METHOD OF MANAGING AND DISPLAYING GENE EXPRESSION DATA

BACKGROUND OF THE INVENTION

1. Field of the Invention

The present invention relates to a method of managing and displaying data, and in particular to a method of managing and displaying gene expression data obtained by gene expression analysis.

2. Background Art

DNA chips and DNA microarrays (hereinafter collectively referred to as "DNA chips") are used as a means of comprehensively analyzing gene expression data. By using DNA chips, it is possible to decode the entire length of a genome sequence, such as a human genome sequence or a mouse genome sequence, although the construction and functioning of genes remain largely unknown.

The probes implemented in DNA chips are determined by information on a genome sequence, but due to cases where it is necessary to consider the influence of splice variants and cases where all of the genes existing in a single species are profiled, the number of probes mounted in DNA chips is steadily increasing.

Since the number of probes that can be implemented in a single DNA chip is limited, at present, experiments are normally carried out in batch units. By doing so, the probes are divided into batch units (the unit for one experiment), and are placed in different DNA chips. When conducting such experiments in batch units, different DNA chips are used for the same samples, so that variations in quality occur between the batch units, which results in the problem of there being overall variations in quality.

Normally, when experiments are carried out on a single sample using different DNA chips, gene expression data is normalized on a DNA chip basis, with it being necessary to determine whether variations in such data are caused by variations in quality, biological variations, or technical variations. The assessment and distinguishing of variations in experiment results are a major issue when interpreting gene expression data. When the variations between batch units are added to the various types of variations mentioned above, it becomes even more difficult to discover the causes of such variations.

Non-Patent Document 1 states that to solve this kind of problem, it is important to draw up an experiment design that sets independent experiment units.

FIG. 1 shows one example of an experiment shown in Non-Patent Document 1. In this experiment, the difference in effect of two treatments A and B on mice is investigated. As a sample, four mice 101 are prepared, with two of the mice being subjected to treatment A and the other two mice being subjected to treatment B. As duplicated specimens, two mRNA extractions are taken from each mouse and are marked with respectively different fluorescent dyes 102, 103. The specimens marked with the fluorescent dye 102 are set as Channel 1 (Ch1) and the specimens marked with the fluorescent dye 103 are set as Channel 2 (Ch2). The four specimens prepared in this way are labeled with the codes A1, A2, B1, B2. The codes of the specimens are respectively composed of a letter showing the treatment and a number of the duplicated specimen subjected to the same treatment. Four specimen pairs that respectively have different treatments and channels are taken from eight specimens, and hybridization is carried out on DNA chips 104.

On the other hand, when the difference in effect of the two treatments A and B on mice is investigated, two mice are provided, and one mouse is subjected to treatment A and the other mouse is subjected to treatment B. mRNA extractions are taken from each mouse, the mRNA extractions are dyed with fluorescent dyes of respectively different colors, and hybridization is carried out on DNA chips. In this method, the experiment data is biased due to bias in the selection of the mice and the properties of the two fluorescent dyes. Accordingly, the resulting experiment data cannot be said to be statistically valid.

In the example shown in FIG. 1, the duplicated samples extracted from the respective mice are subjected to a dye-swap experiment and hybridization is carried out for suitable combinations selected from the duplicated samples mRNA, so that there is a reduction in technical variations. That is, the statistical process disclosed in Non-Patent Document 1 is thought to be effective when analyzing data.

Next, a different example experiment to the example shown in FIG. 1 will be described with reference to FIG. 2. In this example experiment, the difference in effect of a single treatment A on two different cells is investigated. First, as samples, two each of two types of cells, "Normal" cells 201 and "Disease" cells 202, are prepared. All of these cells are subjected to the treatment A, and two mRNA extractions are taken as duplicated specimens from each cell. The specimens from the "Normal" cells 201 and the specimens from the "Disease" cells 202 are marked with respectively different fluorescent dyes 203, 204. The specimens marked with the fluorescent dye 203 are set as channel 1 (Ch1) and the specimens marked with the fluorescent dye 204 are set as channel 2 (Ch2). The four pairs of specimens prepared in this way are labeled with the codes N1, N2, D1, D2. The codes of the specimens are respectively composed of a letter showing the cell type and a number of the duplicated specimen of the same type. Four specimen pairs that respectively have different cells and channels are taken from eight specimens, and hybridization is carried out on DNA chips 205.

This method is often used when comparing control samples (for example, Normal cells) with analyzed samples (for example, Disease cells). This method does not carry out a dye-swap method, but is also used when assessing reproducibility through repeated experiments where the same samples and same chips are used.

To comprehensively carry out various types of experiments with consideration to all of the statistical processes disclosed in Non-Patent Document 1, it is necessary to use a large number of DNA chips in each experiment and there is also an increase in the number of experiments.

On the other hand, the information relating to respective experiments includes information such as experiment conditions, types of samples, numbers of independent samples, treatment methods for the samples, types of DNA chips used, and combinations of marking methods used for hybridization, as well as information such as information on probes mounted on the DNA chips (such as gene information obtained from public databases), the date and times of the experiments, and information on the persons conducting the experiments. To efficiently analyze gene expression data including such a large amount of information, an efficient gene expression data managing system is required.

[Non-Patent Document 1]

Churchill, G. A. (2002) "Fundamentals of Experimental Design for cDNA Microarrays" Nat. Genet. 32 Suppl, p 490-495.

With a conventional gene expression data analyzing system, it is possible to input detailed information on the experiment conditions and the samples as information aside from the gene expression data, but such information is expressed in a tree format or a list format. In a system that displays information in a tree format, data that has been analyzed is managed as a folder and the information is managed without considering information on the experiment conditions or the target specimens. In a system that displays information in list format, individual sets of hybridization information are displayed, but the data is not managed with consideration to experiment conditions in various experiment designs.

For gene expression data obtained from experiments on batch units, it is ultimately necessary to assess the expression values after putting the values on the same basis for analysis as data for the same species.

However, in a conventional gene expression data analyzing system, for experiments conducted in batch units, replicated experiments are displayed through hybridization using duplicated specimens, and display is not carried out with consideration to the dye-swap method for the target.

In a conventional gene expression data analyzing system, it is not possible to additionally display the chip orientation. Accordingly, researchers have to merge gene expression data obtained from different experiments using the same specimens beforehand and to newly generate folders or lists using a conventional gene expression data analyzing system.

When different experiment designs have been drawn up by researchers, a large amount of gene expression data is generated using many DNA chips. However, it has not been possible to visually and understandably display a data management display for replicated experiments and dye-swap experiments that consider hybridization combinations. Accordingly, it has not been possible to smoothly carry out operations such as the verification, pre-processing, and analysis of such data.

SUMMARY OF THE INVENTION

It is an object of the present invention to provide, for gene expression analysis, a method of visually and clearly managing and displaying a large amount of gene expression data obtained based on various experiment designs.

A gene expression data managing and displaying method according to the present invention manages and displays gene expression data including information relating to DNA chips and probes mounted on the DNA chips, gene expression value information obtained by the DNA chips, and experiment information relating to a hybridization experiment,
the method including:
a row setting step that sets a number of rows equal to a number of types of the DNA chips;
an item setting step that determines a subject of analysis in the hybridization experiment and sets, based on the determined subject of analysis, items corresponding to the types of DNA chips;
a column setting step that sets a number of columns equal to the number of items set in the item setting step;
a matrix generating step that generates a matrix composed of a number of rows given by adding one to the number of rows set in the row setting step and a number of columns given by adding one to the number of columns set in the column setting step;
a first column inserting step that inserts the types of DNA chips into respective cells in a first column of the matrix;
a first row inserting step that inserts the items into respective cells in a first row of the matrix;
a cell inserting step that inserts, into respective cells at intersections of columns and rows in the matrix, experiment data for a combination of a type of DNA chip in the row to which a cell belongs and an item in the column to which the cell belongs; and
a matrix drawing step that draws a matrix composed of cells in which the types of DNA chip, the items, and the experiment data have been inserted.

In addition, a user interface in a wizard format for smoothly inputting information is included as a method of obtaining the above information. Also included is a matrix-format data managing display method that displays scatter diagrams using expression data from a display that shows one or a plurality of hybridizations from a data managing/display screen and displays a matrix visually showing, in accordance with a specified experiment condition or in accordance with types of chips, a table characterized by carrying out statistic analysis. Also, a display function that can switch between presenting information in a conventional table format and presenting information in the matrix format is included.

In addition, according to the present invention, a gene expression data managing and displaying method extracts two specimens from each sample, marks all of the extracted specimens with two respectively different fluorescent dyes to identify organisms of the samples or treatments applied to the samples, and in a case where the specimens marked with one of the fluorescent dyes are set as Channel 1 and the specimens marked with another of the fluorescent dyes are set as Channel 2, manages and displays gene expression data including information relating to DNA chips and probes mounted on the DNA chips, gene expression value information obtained by the DNA chips, and experiment information relating to a hybridization experiment,
the method including:
a subject of analysis determining step that compares a number of types of treatment methods for the samples with a number of types of samples, determines that a subject of analysis is to investigate effects of the treatment methods on samples when there are more types of treatment methods for samples than types of samples, and determines that the subject of analysis is to investigate effects due to types of samples when there are not more types of treatment methods for samples than types of samples;
a first column and row setting step that, when the subject of analysis determining step has determined that the subject of analysis is to investigate effects of the treatment methods on samples, a same number of columns as the number of types of treatment methods of Channel 1 and sets a same number of rows as the number of types of treatment methods of Channel 2;
a matrix generating step that generates a matrix composed of a number of rows given by adding one to the number of rows set in the first column and row setting step and a number of columns given by adding one to the number of columns set in the first column and row setting step;
a first column inserting step that inserts the types of treatment methods of Channel 2 into respective cells in a first column of the matrix;
a first row inserting step that inserts the types of treatment methods of Channel 1 into respective cells in a first row of the matrix;
a cell inserting step that inserts, into respective cells at intersections of columns and rows in the matrix, experiment data for a combination of a treatment method in a row to which a cell belongs and a treatment method in a column to which the cell belongs; and a matrix drawing step that draws a matrix composed of cells in which the types of DNA chip, the types of treatment methods, and the experiment data have been inserted.

According to the present invention, even when experiments are carried out in batch units so that the number of probes mounted on DNA chips covers all of the genome sequence information, it is possible to assess various types of gene expression data produced for the same species after putting the data on the same basis for analysis.

Also, it is possible to manage and display data so that time series and types of DNA chips can be readily understood and verified with regard to hybridization combinations, application of a dye-swap method and replicated experiments so that a large amount of complicated gene expression data can be properly ordered.

It is also possible to reduce the time taken to understand and manage the data after the execution of operations, such as comparisons of data or statistical processes, selected from the display of the data managing/display screen, thereby facilitating the analysis of gene expression data.

BRIEF DESCRIPTION OF THE DRAWINGS

FIG. 4 is a diagram showing one example of a data construction for experiment information;

FIG. 5 is a diagram showing one example of a data construction for expression value information;

FIG. 6 is a diagram showing one example of a data construction for probe information;

FIG. 7 is a diagram showing a screen composition for inputting experiment information;

DESCRIPTION OF THE PREFERRED EMBODIMENTS

Figure 3:
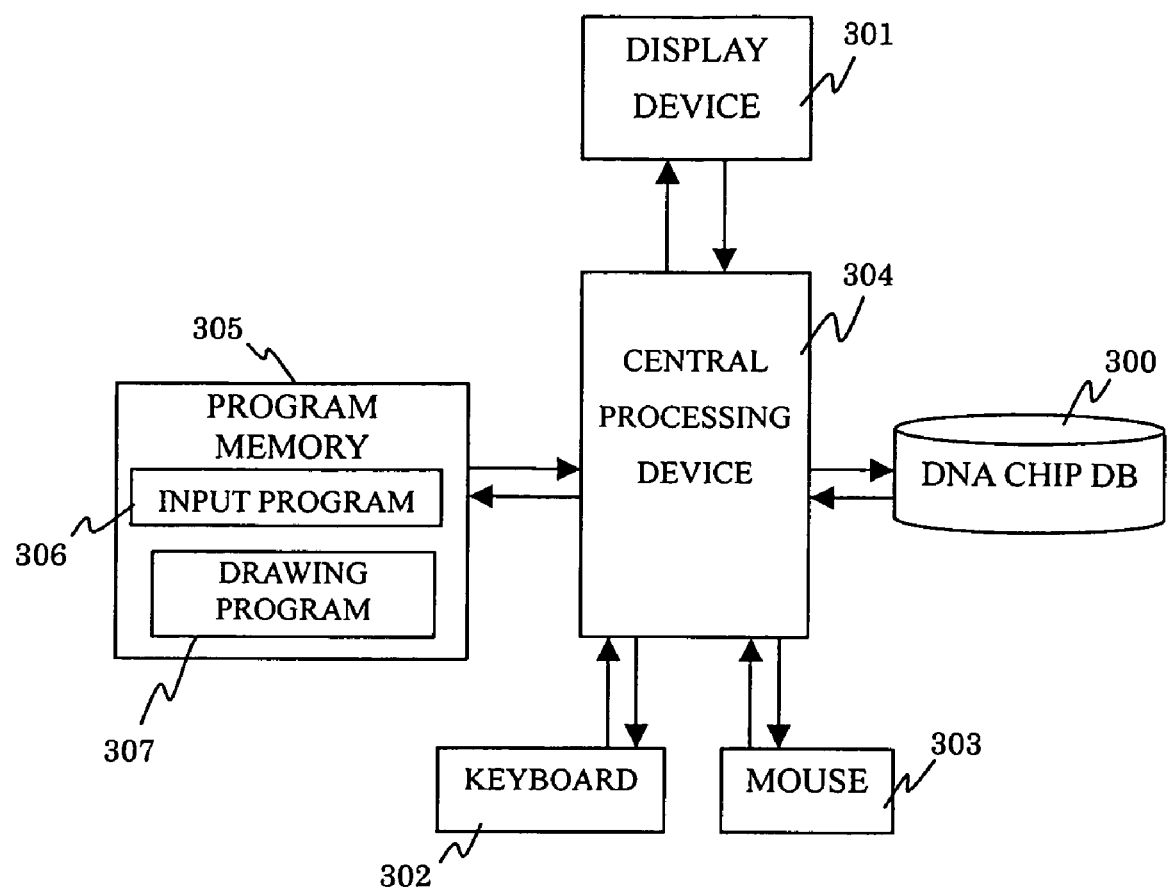
FIG. 3 is a system construction diagram for an apparatus that carries out the gene expression data managing/displaying method according to the present invention.

The present invention will now be described in detail with reference to the attached drawings. FIG. 3 is a diagram showing the system construction of an apparatus for executing a method of managing and displaying gene expression data according to the present invention. The apparatus of the present embodiment includes a DNA chip database 300 in which information relating to DNA chips such as expression value information, experiment information, and probe information is recorded, a display device 301 for displaying a data management window and the like for managing data, a keyboard 302 and a mouse 303 for inputting information related to experiment data and performing selection operations for DNA chip data from the data management window, a central processing device 304, and a program memory 305 that stores programs required for the processing by the central processing device 304. An input program 306 for inputting experiment information and the like and storing the experiment information in the DNA chip database 300 and a drawing program 307 for fetching expression value information, experiment information, probe information, and the like from the DNA chip database 300 and displaying the information are stored in the program memory 305. The expression value information, experiment information, and probe information stored in the DNA chip database 300 will now be described with reference to FIG. 4 to FIG. 6.

FIG. 4 shows an example of the experiment information stored in the DNA chip database 300. Here, it is assumed that the same experiment is carried out as the experiment shown in FIG. 1. That is, four mice are prepared as samples, with two of the mice being subjected to treatment A and the other two mice being subjected to treatment B. As duplicated specimens, two mRNA extractions are taken from each mouse and are marked with one or two types of fluorescent dyes. When the specimens have been marked with two types of fluorescent dyes, the specimens marked with one fluorescent dye are set as Channel 1 (Ch1) and the specimens marked with the other fluorescent dye are set as Channel 2 (Ch2). The four pairs of specimens prepared in this way are labeled with the codes A1, A2, B1, B2. The codes of the specimens are respectively composed of a letter showing the treatment and a number of the duplicated specimen subjected to the same process. Four specimen pairs that respectively have different treatments and channels are taken from eight specimens, and hybridization is respectively carried out on four DNA chips.

It should be noted that in the present embodiment, it is assumed that N hybridization experiments are carried out in a time series using different chip types. For example, four DNA chips are provided for each chip type, and hybridization is carried out on each DNA chip. This is repeated for the number of times given in the time series.

FIG. 4 is a table showing experiment information for N hybridization experiments. Each row in FIG. 4 shows the data of a single hybridization experiment.

A "Hybridization ID" column 400 shows identification codes that are uniquely decided for each hybridization, while a "Repeated Experiment Unit" column 401 shows the number of repetitions for which hybridization has been carried out. A "Chip Type" column 402 shows the type of DNA chip for identifying the DNA chips, with different probes being mounted on DNA chips of different types.

A "Parameter" column 403 shows time, concentration, volume, and the like that is selected as a parameter. When the effects of changes in time, concentration, volume and the like are the subject of analysis, an appropriate parameter is selected from these physical values. In this example, since the experiment is a time series experiment, times are shown in the "Parameter" column 403. When the time, concentration, volume and the like are fixed and the effects of changes in such are not the subject of analysis, this column is blank.

A "Ch1 Treatment Method" column 404 shows the treatment methods carried out on the specimens of Ch1, while a "Ch2 Treatment Method" column 405 shows the treatment methods carried out on the specimens of Ch2. The treatment method columns 404, 405 show environmental factors such as the main types of drugs, chemical substances, heating, cooling, and nutritional status. A "Ch1 Sample" column 406 and a "Ch2 Sample" column 407 show information on samples such as organism type and tissue and cell types.

A "Blocks" column 408 shows the number of blocks in a single DNA chip, and a "Spots" column 409 shows the number of spots per block. By multiplying the number of blocks by the number of spots, the number of probes that can be mounted on a single DNA chip can be found. For example, when the hybridization ID=1, 48×225 probes are mounted on a single DNA chip.

FIG. 5 shows an example of the expression value information stored in the DNA chip database 300. A "Hybridization ID" column 500 corresponds to the "Hybridization ID" column 400 in FIG. 4. As shown in FIG. 5, as one example, there are 48×225 pieces of data for which the hybridization ID equals "1". A "Probe ID" column 501 shows identification information that is uniquely determined for the probes mounted on a DNA chip. A "Ch1 Intensity" column 502 and a "Ch2 Intensity" column" 503 respectively show the hybridization measured values for Channel 1 and the hybridization measured values for Channel 2. Accordingly, expression values corresponding to individual probe IDs are stored in the "Ch 1 Intensity" column 502 and "Ch 2 Intensity" column 503.

FIG. 6 shows an example of probe information stored in the DNA chip database 300. FIG. 6 shows the details of sequence information (normally, in many cases such information is fragments of mRNA), which forms the base for designing probes, corresponding to M probes. A "Probe ID" column 600 corresponds to the "Probe ID" column 501 of FIG. 5. A "Description" column 601 expresses function information in an organism, and an "Accession No. 1" column 602 shows numbers that uniquely identify sequence information and are registered in a public database. An "Accession No. 2" column 603 shows numbers registered in another public database. A "Note 1" column 604 and "Note 2" column 605 show other information relating to probes.

These items 601 to 605 change according to the probe information mounted on a DNA chip and the type of DNA chip used. Normally, in analysis of gene expressions using a DNA chip, the probe information includes information such as detailed information relating to probes, accession numbers for a plurality of public databases (a large variety of, but at most 20 public databases exist), flag information expressing a state of measurement values of fluorescence intensity, functions as proteins within the organism of the sequence information based on which probes are designed, and specific information chosen by users.

FIG. 7 shows an example of an input screen for allowing a user to input the experiment information shown in FIG. 4. A name that identifies, as a single "experiment", a set of gene expression data obtained from hybridization experiments on the same subjects for analysis is entered into an "Experiment Name" box 700 in the top-right part of the screen. By recalling a previous experiment via the "Experiment Name" box 700, a user can refer to data that has been previously imported into the analysis system and reanalyze data.

The various items in the first row of the table displayed below the "Experiment Name" box 700 will now be described. File names of files that store expression data imported into the analysis system are inputted into a "File Name" column 701. A type of DNA chip used in the experiments corresponding to the respective files are entered into a "Chip Type" column 702. This information is stored in the "Chip Type" column 402 of FIG. 4. Information on time series, concentration, volume, and the like are inputted into a "Parameter" column 703. This information is stored in the "Parameter" column 403 of FIG. 4. A treatment method to which the specimens of Ch1 are subjected is entered into a "Ch1 Treatment Method" column 704 and a treatment method to which the specimens of Ch2 are subjected is entered into a "Ch2 Treatment Method" column 705. This information is stored in the "Ch 1 Treatment Method" column 404 and the "Ch 2 Treatment Method" column 405 in FIG. 4.

Information on samples such as the types of organisms and types of tissues and cells relating to the specimens of Ch1 and Ch2 is entered into a "Ch1 Sample" column 706 and a "Ch2 Sample" column 707. This information is stored in the "Ch1 Sample" column 406 and the "Ch 2 Sample" column 407 of FIG. 4.

To verify the reproducibility, repeated experiments are conducted using the same types of samples and the same chip types. In the case of a repeated experiment, a file is selected in the "File Name" box 701 and a "Select Repeated Experiment" button 708 is clicked to add one to the value in the "Repeated Experiment Unit" column 401 of FIG. 4. By clicking a "Cancel Selection" button 709, it is possible to cancel a file that has been registered as a repeated experiment. In this case, the value in the "Repeated Experiment Unit" column 401 of FIG. 4 is decremented. By clicking a radio button 710, the treatment method of the expression data in the repeated experiment is selected.

Cells 711 for entering information for the various items are provided for the respective files. The user directly enters character strings into the cells 711 using the input devices 302, 303, and by clicking a "Fill Down" button 712 can repeatedly enter the same information, which reduces the burden of inputting data.

To enter information aside from the items shown in the first row of the table in FIG. 7, the user clicks an "Add Information" button 713. By doing so, a new column is generated and it becomes possible to enter a new item. At this time, a new item is added to the experiment information data in FIG. 4. By clicking the "Delete" button 714, it is possible to delete unnecessary information from the columns already displayed.

Figure 1:
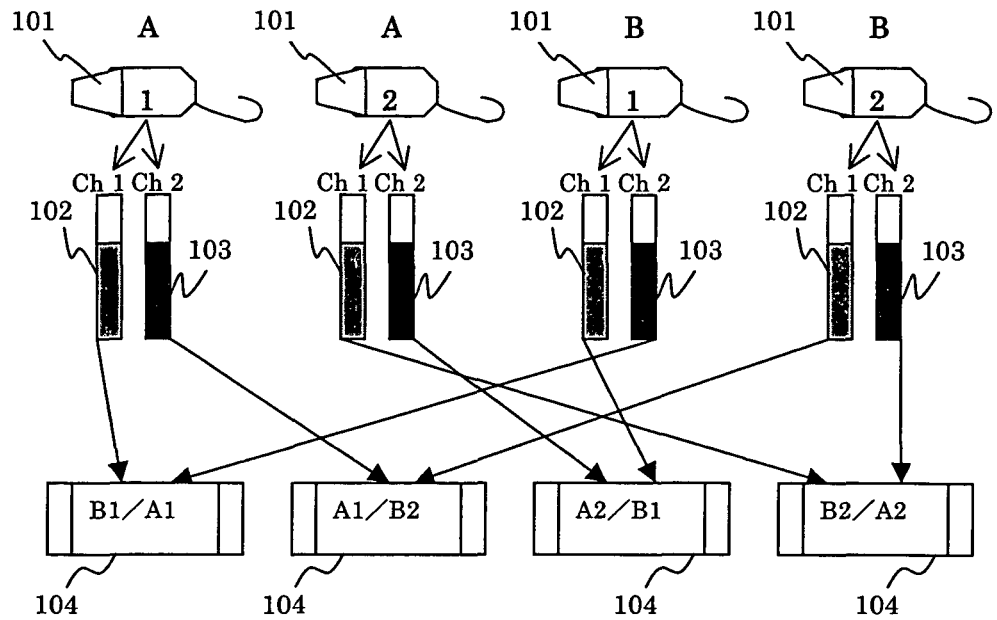
FIG. 1 is a schematic diagram useful in explaining an example of a specimen extraction method and a dye-swap method for comparative experiments for treatment methods.
Figure 8:
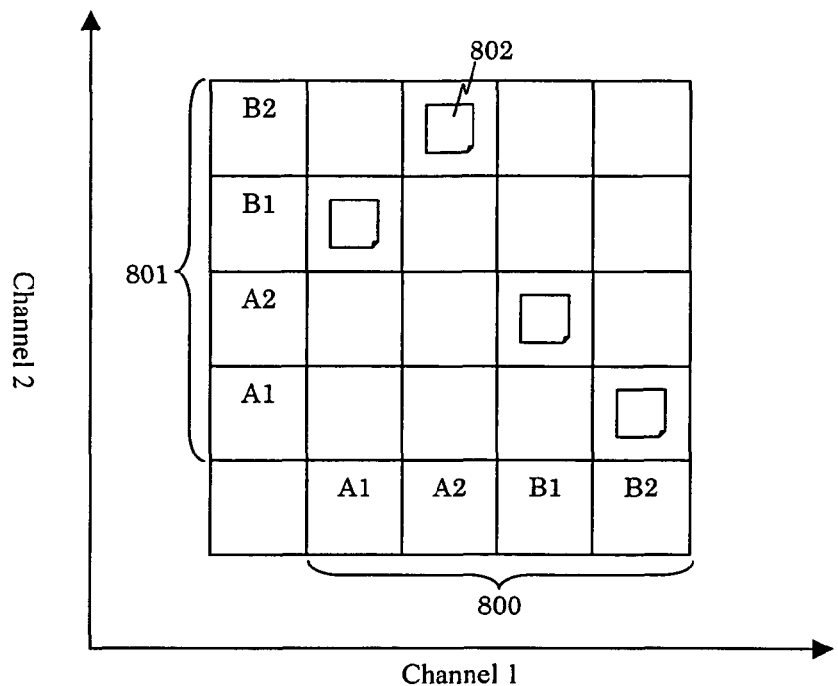
FIG. 8 is a diagram showing an example where the hybridization experiment of FIG. 1 is displayed in a small matrix.

FIG. 8 shows an example of where the data of FIG. 4 is fetched from the DNA chip database 300 and drawn in a matrix on a screen by the gene expression data managing/display method according to the present invention. Here, the experiment shown in FIG. 1 is expressed in the matrix. In the experiment of FIG. 1, treatment A and treatment B are compared using mice. The horizontal axis shows the type of treatment method for Channel 1, Channel 1 being mRNA extractions identified by the first fluorescent dye 102, and the vertical axis shows the type of treatment method for Channel 2, Channel 2 being mRNA extractions identified by the second fluorescent dye 103. The codes of the Channel 1 specimens are shown in the bottom row 800 of the matrix and the codes of the Channel 2 specimens are shown in the leftmost row 801 of the matrix. The files shown inside the cells of the matrix show expression data for hybridization carried out on the Channel 1 specimen indicated on the horizontal axis and the Channel 2 specimen indicated on the vertical axis. For example, a file 802 shows expression data for hybridization carried out on the combination of the Channel 1 specimen A2 and the Channel 2 specimen B2.

Figure 2:
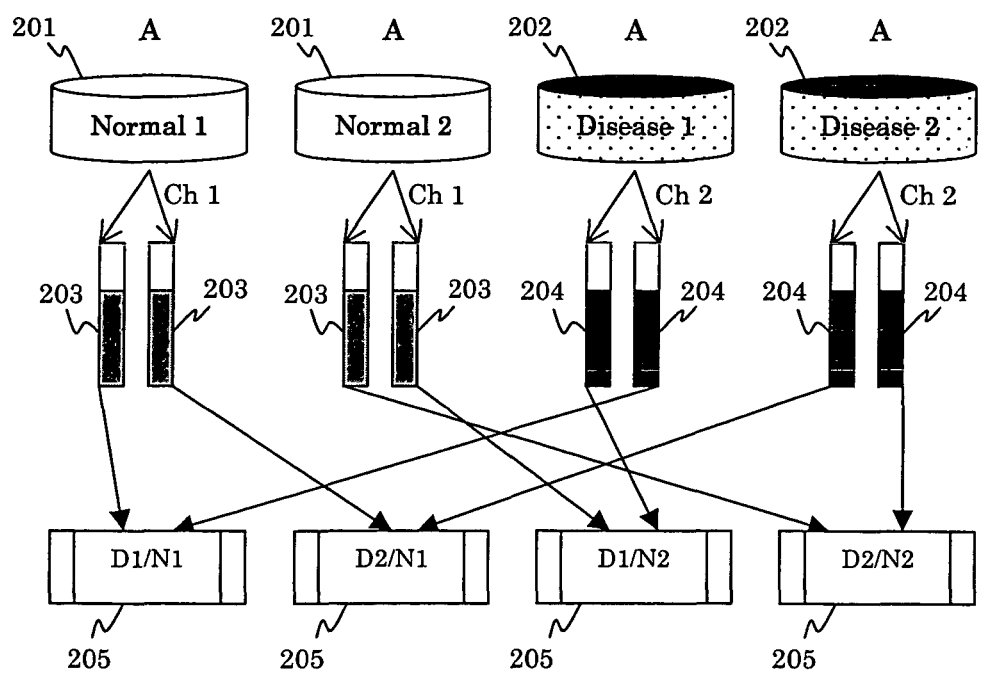
FIG. 2 is a schematic diagram useful in explaining an example of a specimen extraction method and replicated experiments for comparative experiments for types of specimens.
Figure 9:
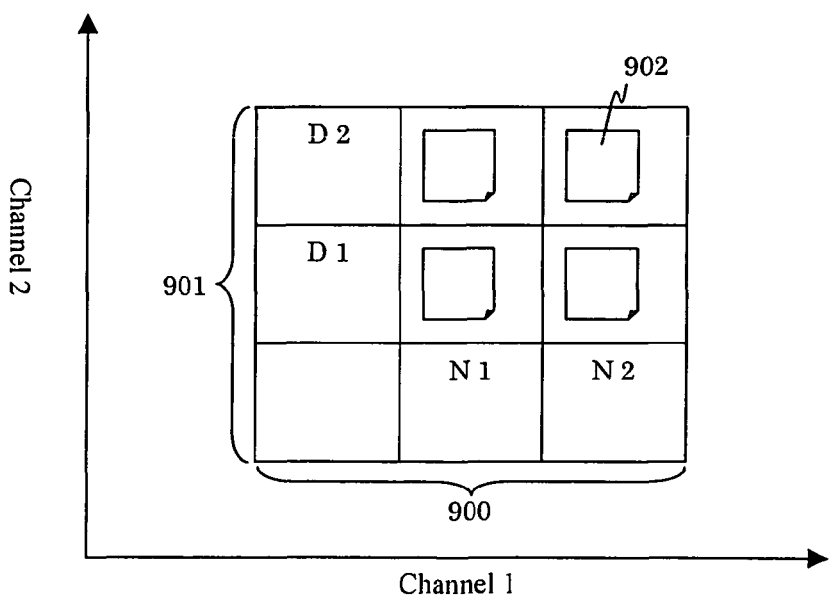
FIG. 9 is a diagram showing an example where the hybridization experiment of FIG. 2 is displayed in a small matrix.

In FIG. 9, the experiment shown in FIG. 2 is expressed in a matrix by the gene expression data managing/displaying method according to the present invention. In the experiment of FIG. 2, normal cells are compared with diseased cells. The horizontal axis shows the Channel 1 specimens, that is, the normal cells 201 marked with the first fluorescent dye 203, while the vertical axis shows the Channel 2 specimens, that is, the diseased cells 202 marked with the second fluorescent dye 204. The codes of the Channel 1 specimens are shown in the bottom row 900 of the matrix and the codes of the Channel 2 specimens are shown in the leftmost column 901 of the matrix. The files shown inside the cells of the matrix show expression data for hybridization carried out on the Channel 1 specimen indicated on the horizontal axis and the Channel 2 specimen indicated on the vertical axis. For example, a file 902 shows expression data for hybridization carried out on the combination of the Channel 1 specimen N2 and the Channel 2 specimen D2.

Figure 10:
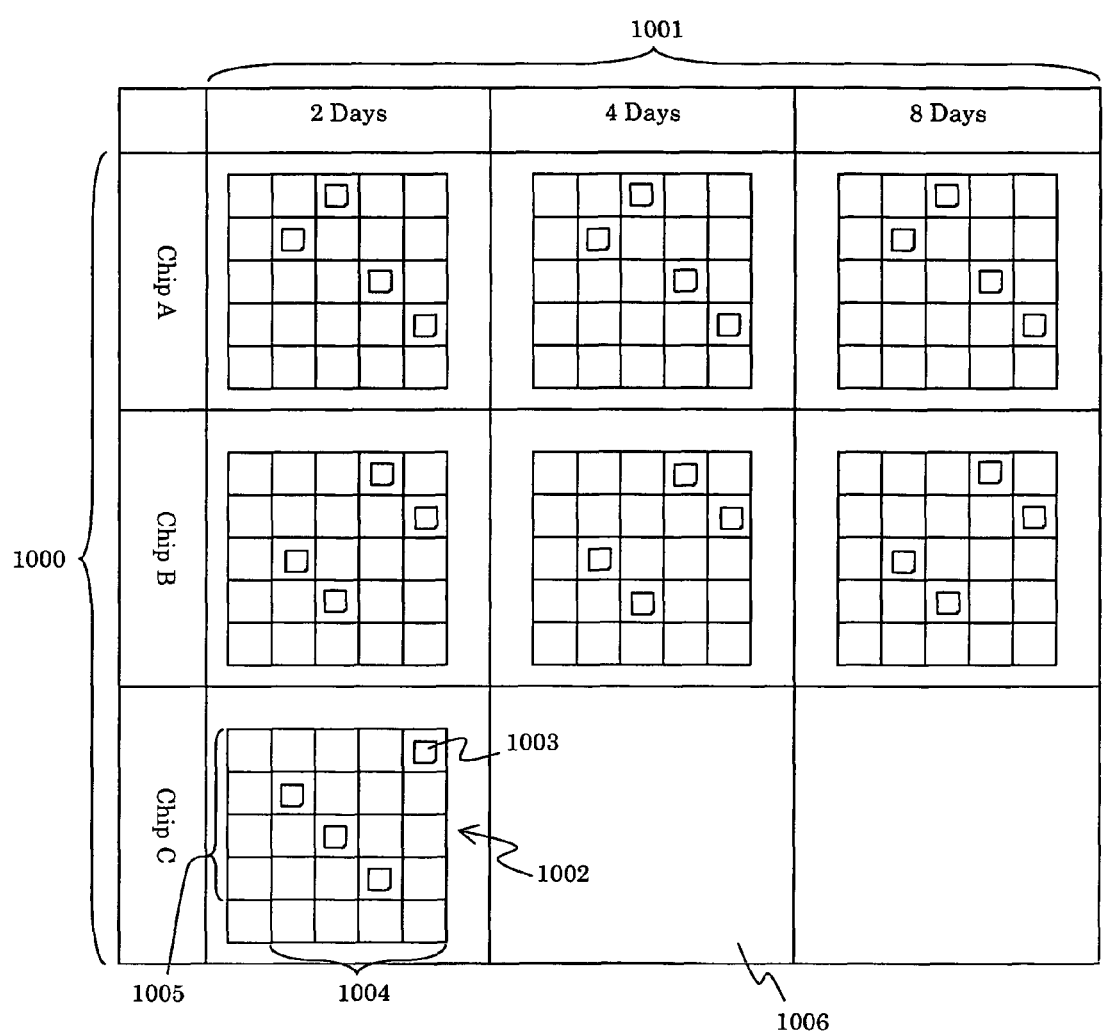
FIG. 10 is a diagram showing the composition of a data management display displayed according to the gene expression data managing/displaying method according to the present invention.

FIG. 10 shows an example of where the results of a hybridization experiment are displayed in a matrix by the gene expression data managing/displaying method according to the present invention. In the example experiment shown in FIG. 1, four DNA chips of the same type are used for four mice, and hybridization that uses the dye-swap method is repeatedly carried out. In the present example, the same kind of experiment is carried out using three types of DNA chips in a time series.

The chip types are shown in the leftmost column 1000 of the matrix and the times in the time series are shown in the top row 1001 of the matrix. As described with reference to FIG. 4, when the subject of analysis is the effect of changes in a parameter such as time, concentrations, and volume, a suitable physical value is selected from such physical values and set as the parameter. The selected parameter such as time, concentration, and volume is displayed in the top row 1001.

When the subject of analysis is not the effects of changes in a parameter such as time, concentration, and volume, that is, when the "Parameter" column 403 of the experiment information in FIG. 4 is blank, the top row 1001 shows combinations of treatment methods for the samples of the two channels or combinations of the types of samples. Accordingly, when the subject of analysis differs according to the experiment, the items in the top row 1001 change.

The small matrices displayed inside the cells of the matrix are the matrix shown in FIG. 8 or FIG. 9. For example, the small matrix 1002 shows the results of an experiment carried out using Chip C with "2 Days" as the conditions.

As was described with reference to FIG. 8 and FIG. 9, the item names of Channel 1 are shown in the bottom row 1004 of the small matrix 1002 and the item names of Channel 2 are shown in the leftmost column 1005. The file 1003 inside a cell in the small matrix 1002 shows expression data for one hybridization carried out on the Channel 1 specimen indicated on the horizontal axis and the Channel 2 specimen indicated on the vertical axis.

The cell 1006 in the matrix is blank. This shows that data is yet to be registered. In the present embodiment, the type of DNA chips and parameters are expressed by the vertical axis and the horizontal axis, and small matrices are displayed in the cells of the matrix. Accordingly, the vertical axis and horizontal axis match the expression format called a "color map" in which expression values are expressed by colors, and it is possible to readily understand the management of chip data.

Figure 11:
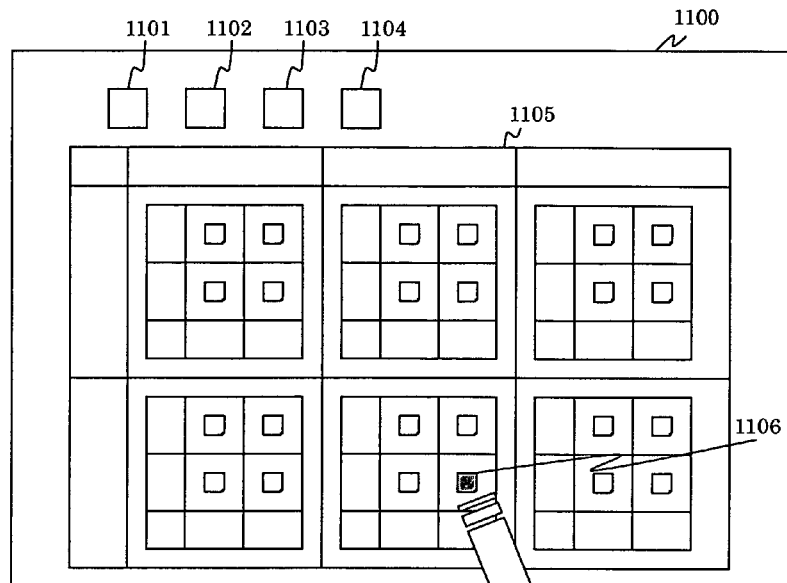
FIG. 11A and FIG. 11B are diagrams showing the functions of data management and display according to the gene expression data managing/displaying method according to the present invention.
Figure 11:
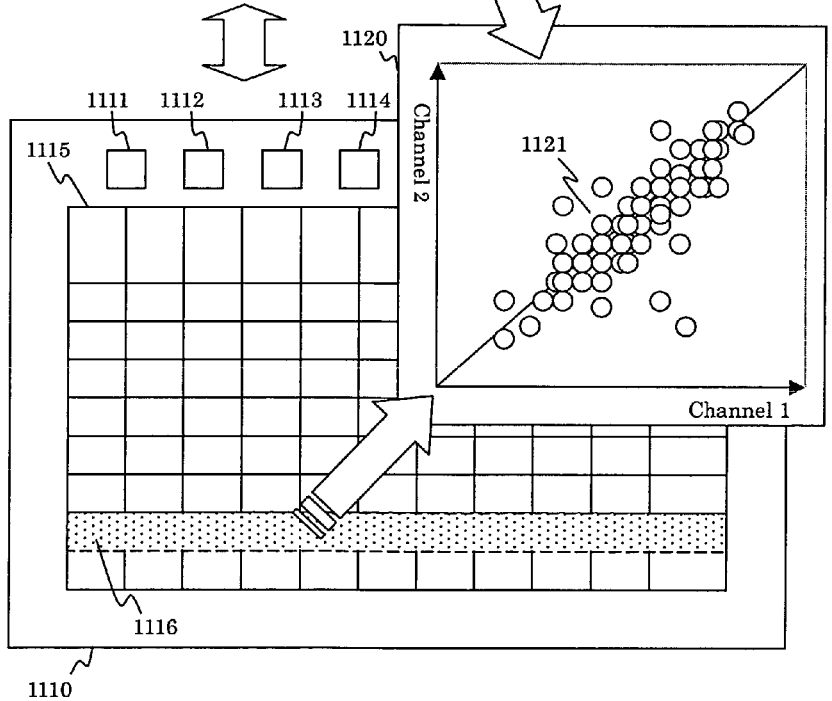

Next, examples of data managing/displaying screens displayed by the display device 301 will be described with reference to FIG. 11A and FIG. 11B. In the present embodiment, it is possible to display a data managing/display screen 1100 as shown in FIG. 11A in which data is visualized or a data managing/display screen 1110 as shown in FIG. 11B in which data is listed, with it being possible to switch between the respective screens. The visualized data managing/display screen 1100 includes a display switching button 1101, a statistical analysis button 1102, an expression data preprocessing button 1103, an expression data normalization button 1104, and a matrix 1105. The matrix 1105 corresponds to the matrix shown in FIG. 10.

In the same way, the list-display data managing/display screen 1110 includes a display switching button 1111, a statistical analysis button 1112, an expression data preprocessing button 1113, an expression data normalization button 1114, and a table 1115. The table 1115 is a table showing the data in the matrix 1105.

By clicking the display switching buttons 1101, 1111, it is possible to switch between the visualized data managing/display screen 1100 and the list-display data managing/display screen 1110. By respectively pressing the statistical analysis buttons 1102, 1112, the expression data preprocessing buttons 1103, 1113, and the expression data normalization buttons 1104, 1114, files showing a plurality of hybridizations can be selected and predetermined treatments can be executed.

By double clicking on a file 1106 showing a single hybridization inside a small matrix in the visualized data managing/display screen 1100, or by double clicking on a row 1116 showing a single hybridization in the list-display data managing/display screen 1110, it is possible to display a scatter diagram showing the expression data in two dimensions in a new window 1120. Each point 1121 in the scatter diagram shows the ratio between the expression values of Channel 1 and Channel 2 for a selected hybridization.

Figure 12:
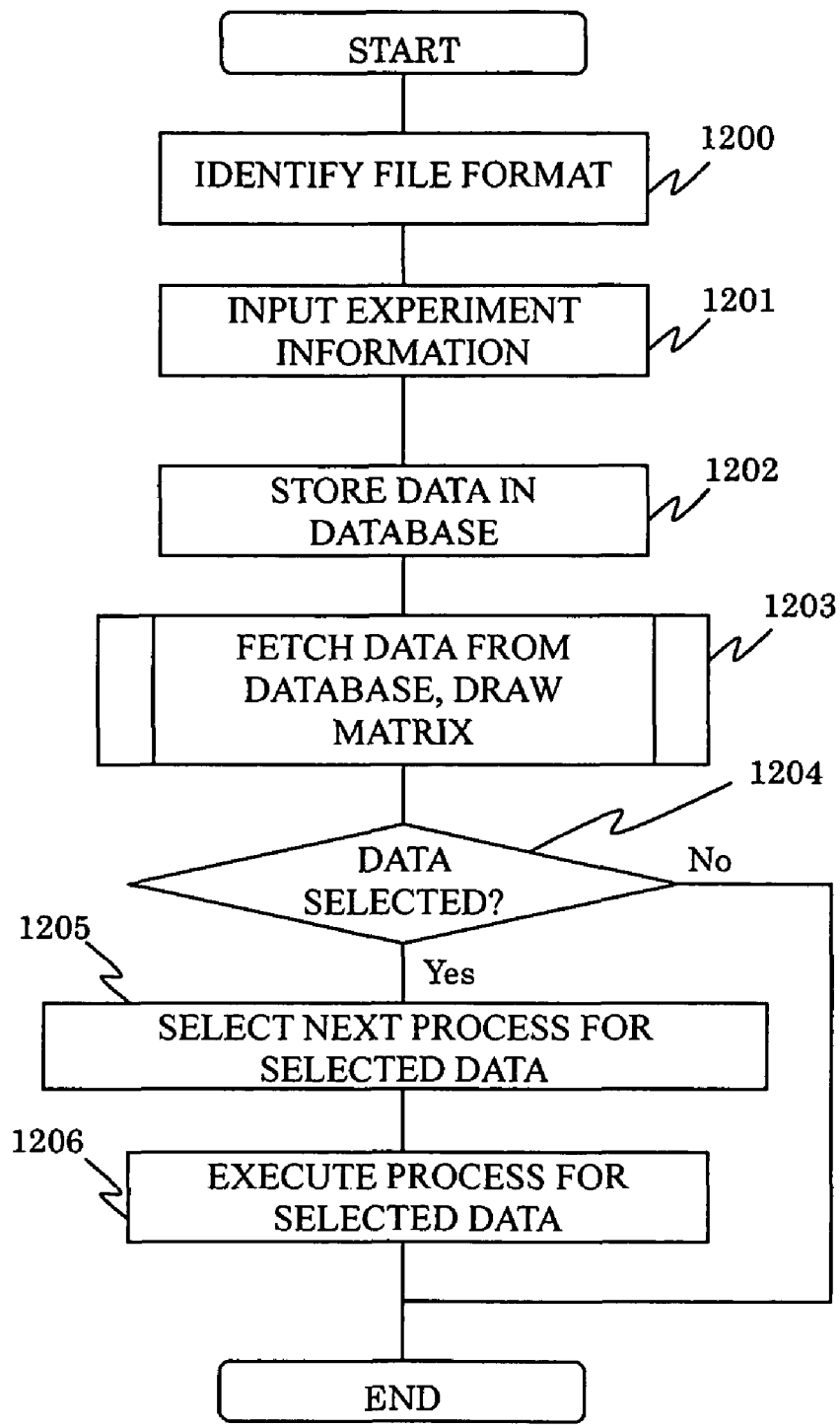
FIG. 12 is a flowchart schematically showing the process of the gene expression data managing/displaying method according to the present invention.

FIG. 12 is a flowchart schematically showing the processing by the present invention. In step 1200, the file format is identified for the file in which expression data imported into the analysis system is stored. Next, in step 1201, the experiment information is inputted. The experiment information is inputted by the user via the input screen shown in FIG. 7. In step 1202, a file in which the expression data produced by measuring hybridization intensity, the inputted experiment information, and the probe information are written is read and is respectively stored in the DNA chip database 300.

In step 1203, the required data is fetched from the DNA chip database 300 and a matrix is drawn based on this information. By doing so, the visualized data managing/display screen 1100 shown in FIG. 11A is displayed by a display device 301. In step 1204, it is determined whether the user has selected data. As described above, it is possible to select the data to be used in the next analysis by double clicking a file in a small matrix using the input device 303. When the user has not selected data, the processing ends.

After selecting the data, the user next clicks the statistical analysis button 1102, the expression data preprocessing button 1103, the expression data normalization button 1104, or the like to select the next analysis. In step 1205, the next process is selected based on the clicked button. In step 1206, the selected process is carried out.

Figure 13:
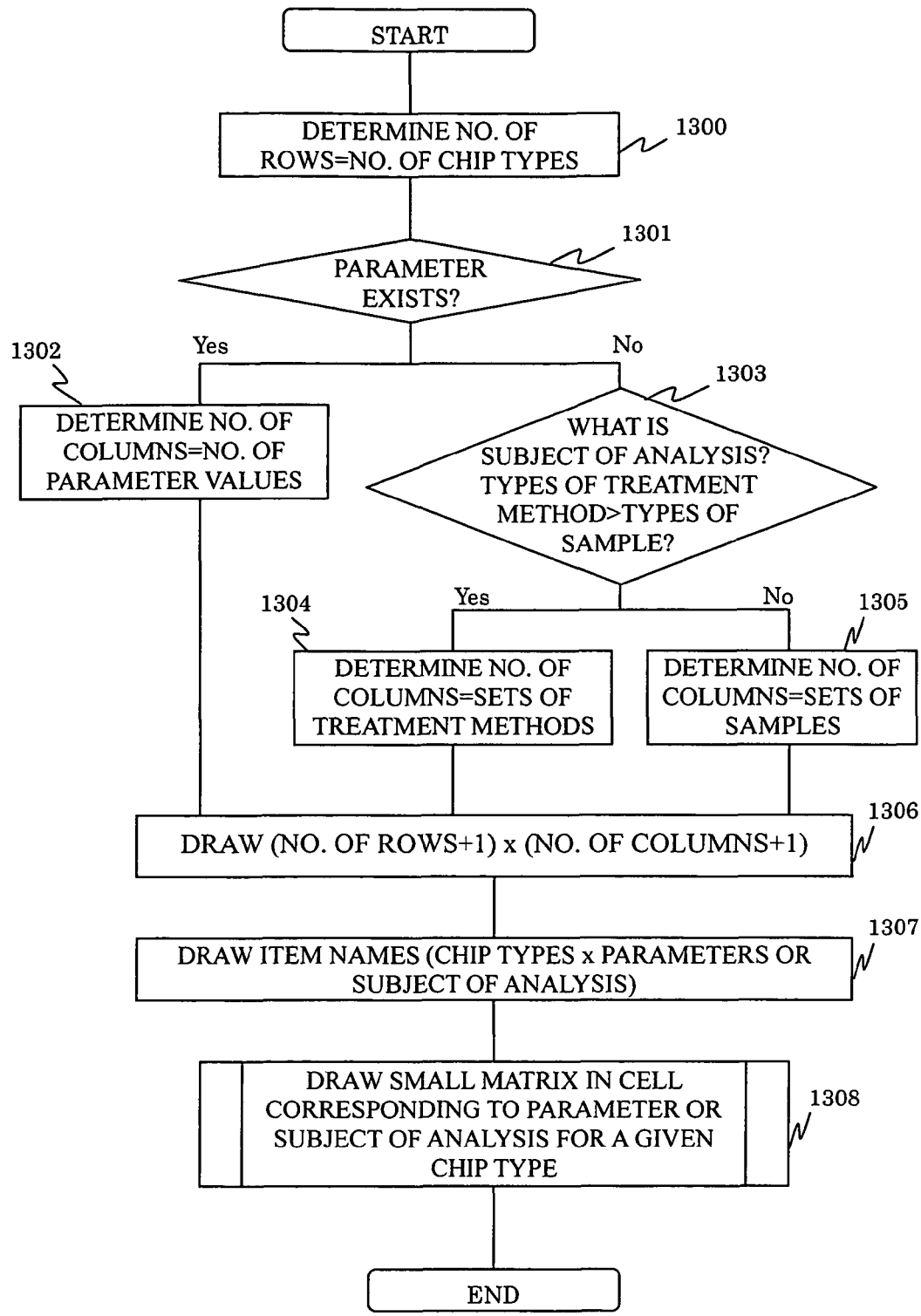
FIG. 13 is a flowchart showing the process for drawing a matrix according to the gene expression data managing/displaying method according to the present invention.

FIG. 13 is a flowchart showing a process in step 1203 in FIG. 12 that fetches data from the DNA chip database 300, determines the items in the leftmost row 1000 and the items in the top row 1001 in FIG. 10, and draws a matrix.

In step 1300, the same number of rows as the number of types in the "Chip Type" column 402 in FIG. 4 is set. In step S1301, it is determined whether values exist in the "Parameter" column 403 in the experiment information in FIG. 4.

That is, it is determined whether the effects of changes in a parameter are the subject of analysis. When values exist in the "Parameter" column 403, the processing proceeds to step 1302 where the same number of columns as the number of values taken by the parameter are set. For example, for a time series experiment, the same number of columns as times in the time series is set. When no values exist in the "Parameter" column 403, the processing proceeds to step 1303, where it is determined whether there are more types of treatment methods than types of samples to investigate whether the subject for comparison and analysis is differences between treatment methods for a sample or differences between types of samples. When there are more types of treatment methods than types of samples, it is determined that the differences between treatment methods for the same sample are to be analyzed, while on the other hand, when there are fewer types of treatment methods than types of samples, it is determined that the differences between samples for the treatment are to be compared.

For example, in the example in FIG. 1, there are two types of treatment methods, A and B, with the types of samples being one type of mouse, so that there are more types of treatment methods than types of samples. Accordingly, as described above, the experiment in FIG. 1 has an object of investigating the differences in the effects of the two treatments A and B on the samples (mice). On the other hand, in the example in FIG. 2, there is only one type of treatment method, treatment A, and two types of cells as the types of samples, so that there are fewer types of treatment methods than types of samples. Accordingly, as described above, the experiment of FIG. 2 has an object of investigating the difference in effect of the single treatment A on two types of samples (cells).

When there are more types of treatment methods than types of samples, the processing proceeds to step 1304 where the same number of columns as the number of sets of treatment method types (where two types form one set) are set. When there are not more types of treatment methods than types of samples, the processing proceeds to step 1305, where the same number of columns as the number of sets of sample types (where two types form one set) are set. In step 1306, one row and one column for displaying item names are added to the set rows and columns, and a (rows+1) by (columns+1) matrix is drawn. In step 1307, the chip types are written in the first column of the matrix and the parameters, the treatment methods for samples, or the sample types are written in the first row. In step 1308, in the cell where the row of the predetermined chip type and a predetermined column intersect, a small matrix such as that shown in FIG. 10 is drawn.

Figure 14:
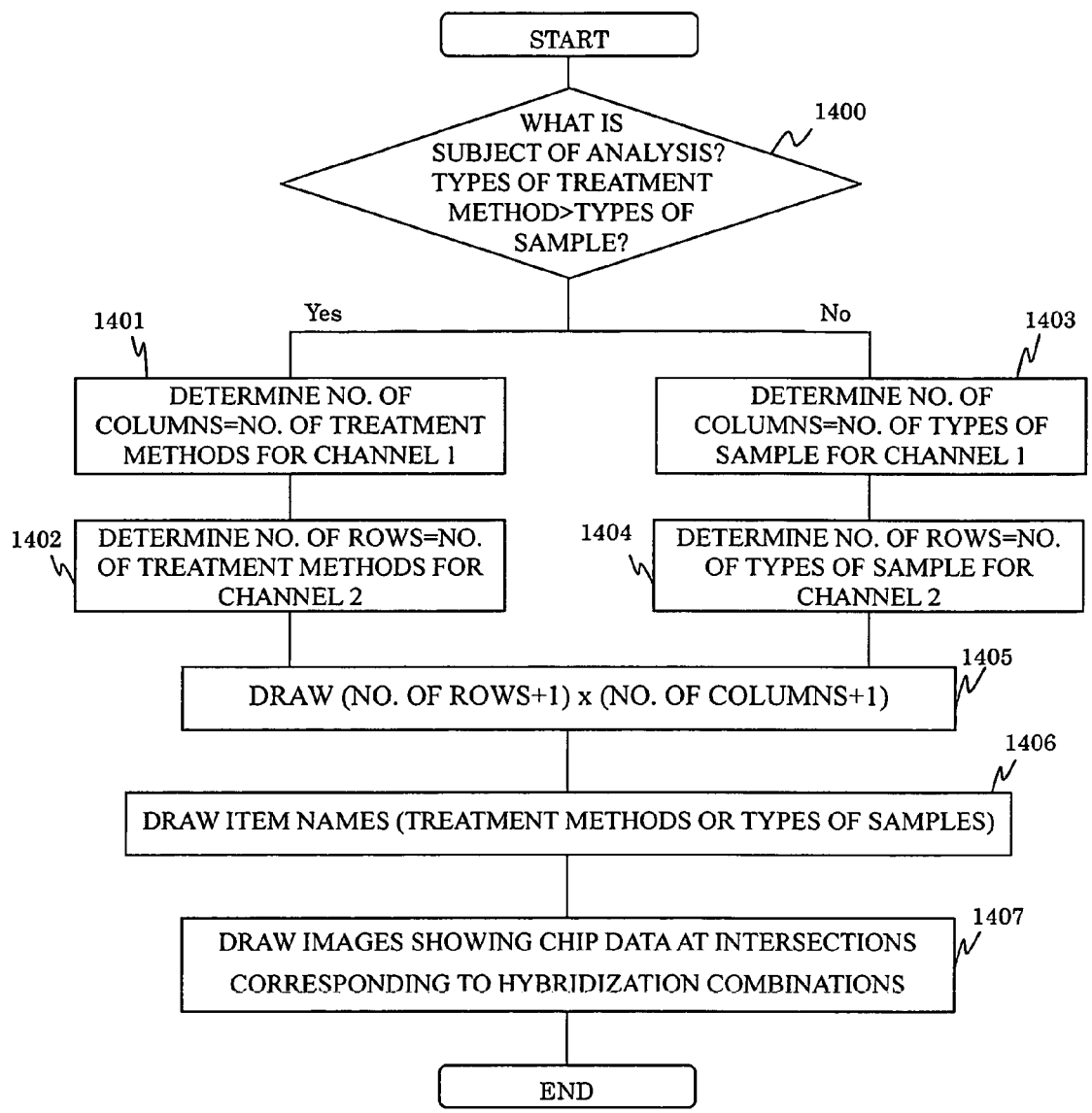
FIG. 14 is a flowchart showing the process for drawing a small matrix according to the gene expression data managing/displaying method according to the present invention.

FIG. 14 is a flowchart showing the drawing procedure for the small matrix in step 1308 in FIG. 13. To display item names of the subject of comparison in the small matrix, first the subject of analysis aside from parameters is investigated from information in the DNA chip database 300. This means that in step 1400, it is determined whether there are more types of treatment methods than types of samples. When there are more types of treatment methods than types of samples, it is assumed that the differences between treatment methods for the same sample are being compared. Conversely, when there are fewer types of treatment methods than types of samples, it is determined that differences between types of samples are being compared.

When there are more types of treatment methods for samples than there are types of samples, the processing proceeds to step 1401 where the same number of columns as the number of types of treatment methods for Channel 1 is set. In step S1402, the same number of rows as the number of types of treatment methods for Channel 2 is set. When there are not more types of treatment methods than there are types of samples, the processing proceeds to step 1403 where the same number of columns as the number of individual samples or the number of types of samples for Channel 1 is set. In step S1404, the same number of rows as the number of types of samples for Channel 2 is set.

In step 1405, one row and one column for displaying item names are respectively added to the set rows and columns, and a (rows+1)×(columns+1) matrix is drawn. In step 1406, Channel 1 is set as the bottom row, Channel 2 is set as the vertical axis, and the combinations of the treatment methods and the combinations of sample types are respectively written in the respective channels. In step 1407, the drawing of images showing chip data is carried out at intersections corresponding to hybridization combinations in the matrix.

What is claimed is:

1. A gene expression data managing and displaying method that manages and displays gene expression data including information relating to DNA chips and probes mounted on the DNA chips, gene expression value information obtained by the DNA chips, and experiment information relating to a hybridization experiment, comprising:

a row setting step that sets a number of rows equal to a number of types of the DNA chips;

an item setting step that determines a subject of analysis in the hybridization experiment and sets, based on the determined subject of analysis, items corresponding to the types of DNA chips, the item setting step including:

a subject of analysis determining step that determines whether the subject of analysis is to investigate bias effects of changes in a parameter on samples, to investigate bias effects of treatment methods on samples, or to investigate bias effects due to types of samples, wherein the subject of analysis determining step compares, when information relating to a parameter is not included in the experiment information relating to the hybridization experiment, a number of types of treatment methods for the samples with a number of types of samples, determines that the subject of analysis is to investigate effects of the treatment methods on samples when there are more types of treatment methods for samples than types of samples, and determines that the subject of analysis is to investigate effects due to types of samples when there are not more types of treatment methods for samples than types of samples; and an item selecting step that selects values to be taken by a parameter as the items when the subject of analysis is to investigate the bias effects of changes in the parameter on samples, selects combinations of types of treatment methods for samples as the items when the subject of analysis is to investigate the bias effects of the treatment methods on samples, and selects combinations of types of samples as the items when the subject of analysis is to investigate effects due to types of samples;

a column setting step that sets a number of columns equal to the number of items set in the item setting step;

a matrix generating step that generates a matrix composed of a number of rows given by adding one to the number of rows set in the row setting step and a number of columns given by adding one to the number of columns set in the column setting step;

a first column inserting step that inserts the types of DNA chips into respective cells in a first column of the matrix;

a first row inserting step that inserts the items into respective cells in a first row of the matrix;

a cell inserting step that inserts a small matrix, into respective cells at intersections of columns and rows in the matrix, said small matrix containing experiment data for a combination of one non-subject of analysis in the row to which the cell belongs and another non-subject of analysis in the column to which the cell belongs;

a matrix drawing step that draws the matrix composed of cells showing the types of DNA chips, the determined subject of analysis, and said small matrices inserted with the experiment data; and a matrix displaying step that display the drawn matrix, wherein the cell inserting step inserts, into the respective cell, an image of said small matrix containing experiment data, for a combination of one of said types of DNA chips in the row to which the cell belongs and a corresponding value of the determined subject of analysis in the column to which the cell belongs.

2. A gene expression data managing and displaying method according to claim 1, wherein the subject of analysis determining step determines that the subject of analysis is to investigate effects of changes in a parameter when information relating to a parameter is included in the experiment information relating to the hybridization experiment.

3. A gene expression data managing and displaying method according to claim 1, further comprising a switching step that switches, when a display switching instruction has been inputted, from a matrix display screen in which the matrix drawn by the matrix drawing step is displayed to a list display screen displaying a table in which the types of DNA chips, the items, and the experiment data have been inserted.

4. A gene expression data managing and displaying method according to claim 1, wherein when an instruction that selects a predetermined cell out of the cells in the matrix is inputted, a scatter diagram for gene expression data included in the experiment data for a combination of the type of DNA chip of the row to which the predetermined cell belongs and the item of the column to which the predetermined cell belongs is displayed.

5. A gene expression data managing and displaying method that extracts two specimens from each sample, marks all of the extracted specimens with two respectively different fluorescent dyes to identify organisms of the samples or treatment methods applied to the samples, and in a case where the specimens marked with one of the fluorescent dyes are set as Channel 1 and the specimens marked with another of the fluorescent dyes are set as Channel 2, manages and displays gene expression data including information relating to DNA chips and probes mounted on the DNA chips, gene expression value information obtained by the DNA chips, and experiment information relating to a hybridization experiment, the method comprising:

a subject of analysis determining step that compares a number of types of treatment methods for the samples with a number of types of samples, determines that the subject of analysis is to investigate effects of the treatment methods on samples when there are more types of treatment methods for samples than types of samples, and determines that the subject of analysis is to investigate effects due to types of samples when there are not more types of treatment methods for samples than types of samples;

a first column and row setting step that sets, when the subject of analysis determining step has determined that the subject of analysis is to investigate effects of the treatment methods on samples, a same number of columns as the number of types of treatment methods of Channel 1 and sets a same number of rows as the number of types of treatment methods of Channel 2;

a matrix generating step that generates a matrix composed of a number of rows given by adding one to the number of rows set in the first column and row setting step and a number of columns given by adding one to the number of columns set in the first column and row setting step;

a first column inserting step that inserts the types of treatment methods of Channel 2 into respective cells in a first column of the matrix;

a first row inserting step that inserts the types of treatment methods of Channel 1 into respective cells in a first row of the matrix;

a cell inserting step that inserts, into respective cells at intersections of columns and rows in the matrix, experiment data for a combination of a treatment method in the row to which the cell belongs and a treatment method in the column to which the cell belongs; and a matrix drawing step that draws a matrix composed of cells in which the types of DNA chip, the types of treatment methods, and the experiment data have been inserted.

6. A gene expression data managing and displaying method according to claim 5, further comprising:

a second column and row setting step that sets, when the subject of analysis determining step has determined that the subject of analysis is to investigate effects due to types of samples, a same number of columns as the number of types of samples of Channel 1 and sets a same number of rows as the number of types of samples of Channel 2;

the matrix generating step that generates a matrix composed of a number of rows given by adding one to the number of rows set in the second column and row setting step and a number of columns given by adding one to the number of columns set in the second column and row setting step;

the first column inserting step that inserts the types of samples of Channel 2 into respective cells in a first column of the matrix;

the first row inserting step that inserts the types of samples of Channel 1 into respective cells in a first row of the matrix;

the cell inserting step that inserts, into respective cells at intersections of columns and rows in the matrix, experiment data for a combination of a type of sample in a row to which a cell belongs and a type of sample in a column to which the cell belongs; and the matrix drawing step that draws a matrix composed of cells in which the types of DNA chip, the types of sample, and the experiment data have been inserted.

7. A computer-readable program embedded in a computer-readable storage medium executable by a computer to carry out a gene expression data managing and displaying method, comprising:

a row setting module that sets a number of rows equal to a number of types of the DNA chips;

an item setting module that determines a subject of analysis in the hybridization experiment and sets, based on the determined subject of analysis, items corresponding to the types of DNA chips, the item setting module including:

a subject of analysis determining module that determines whether the subject of analysis is to investigate bias effects of changes in a parameter on samples, to investigate bias effects of treatment methods on samples, or to investigate bias effects due to types of samples, wherein the subject of analysis determining module compares, when information relating to a parameter is not included in the experiment information relating to the hybridization experiment, a number of types of treatment methods for the samples with a number of types of samples, determines that the subject of analysis is to investigate effects of the treatment methods on samples when there are more types of treatment methods for samples than types of samples, and determines that the subject of analysis is to investigate effects due to types of samples when there are not more types of treatment methods for samples than types of samples; and an item selecting module that selects values to be taken by a parameter as the items when the subject of analysis is to investigate the bias effects of changes in the parameter on samples, selects combinations of types of treatment methods for samples as the items when the subject of analysis is to investigate the bias effects of the treatment methods on samples, and selects combinations of types of samples as the items when the subject of analysis is to investigate effects due to types of samples;

a column setting module that sets a number of columns equal to the number of items set by the item setting module;

a matrix generating module that generates a matrix composed of a number of rows given by adding one to the number of rows set by the row setting module and a number of columns given by adding one to the number of columns set by the column setting module;

a first column inserting module that inserts the types of DNA chips into respective cells in a first column of the matrix;

a first row inserting module that inserts the items into respective cells in a first row of the matrix;

a cell inserting module that inserts, a small matrix, into respective cells at intersections of columns and rows in the matrix, said small matrix containing experiment data for a combination of one non-subject of analysis in the row to which the cell belongs and another non-subject of analysis in the column to which the cell belongs;

a matrix drawing module that draws the matrix composed of cells showing the types of DNA chips, the determined subject of analysis, and said small matrices inserted with the experiment data; and a matrix displaying module that displays the drawn matrix.

8. A computer-readable storage medium storing with a program executable by a computer to carry out a gene expression data managing and displaying method comprising:

a row setting module that sets a number of rows equal to a number of types of the DNA chips;

an item setting module that determines a subject of analysis in the hybridization experiment and sets, based on the determined subject of analysis, items corresponding to the types of DNA chips, the item setting module including:

a subject of analysis determining module that determines whether the subject of analysis is to investigate bias effects of changes in a parameter on samples, to investigate bias effects of treatment methods on samples, or to investigate bias effects due to types of samples, wherein the subject of analysis determining module compares, when information relating to a parameter is not included in the experiment information relating to the hybridization experiment, a number of types of treatment methods for the samples with a number of types of samples, determines that the subject of analysis is to investigate effects of the treatment methods on samples when there are more types of treatment methods for samples than types of samples, and determines that the subject of analysis is to investigate effects due to types of samples when there are not more types of treatment methods for samples than types of samples; and an item selecting module that selects values to be taken by a parameter as the items when the subject of analysis is to investigate the bias effects of changes in the parameter on samples, selects combinations of types of treatment methods for samples as the items when the subject of analysis is to investigate the bias effects of the treatment methods on samples, and selects combinations of types of samples as the items when the subject of analysis is to investigate effects due to types of samples;

a column setting module that sets a number of columns equal to the number of items set by the item setting module;

a matrix generating module that generates a matrix composed of a number of rows given by adding one to the number of rows set by the row setting module and a number of columns given by adding one to the number of columns set by the column setting module;

a first column inserting module that inserts the types of DNA chips into respective cells in a first column of the matrix;

a first row inserting module that inserts the items into respective cells in a first row of the matrix;

a cell inserting module that inserts, a small matrix, into respective cells at intersections of columns and rows in the matrix, said small matrix containing experiment data for a combination of one non-subject of analysis in the row to which the cell belongs and another non-subject of analysis in the column to which the cell belongs;

a matrix drawing module that draws the matrix composed of cells showing the types of DNA chips, the determined subject of analysis, and said small matrices inserted with the experiment data; and a matrix displaying module that display the drawn matrix.

9. A gene expression data managing and displaying method that manages and displays gene expression data including information relating to DNA chips and probes mounted on the DNA chips, gene expression value information obtained by the DNA chips, and experiment information relating to a hybridization experiment, the method comprising:

a row setting step that sets a number of rows equal to a number of types of the DNA chips;

an item setting step that determines a subject of analysis in the hybridization experiment and sets, based on the determined subject of analysis, items corresponding to the types of DNA chips, the item setting step comprising:

a subject of analysis determining step that determines whether the subject of analysis is to investigate effects of changes in a parameter on samples, to investigate effects of treatment methods on samples, or to investigate effects due to types of samples, wherein the subject of analysis determining step compares, when information relating to a parameter is not included in the experiment information relating to the hybridization experiment, a number of types of treatment methods for the samples with a number of types of samples, determines that the subject of analysis is to investigate effects of the treatment methods on samples when there are more types of treatment methods for samples than types of samples, and determines that the subject of analysis is to investigate effects due to types of samples when there are not more types of treatment methods for samples than types of samples; and an item selecting step that selects values to be taken by a parameter as the items when the subject of analysis is to investigate the effects of changes in the parameter on samples, selects combinations of types of treatment methods for samples as the items when the subject of analysis is to investigate effects of the treatment methods on samples, and selects combinations of types of samples as the items when the subject of analysis is to investigate effects due to types of samples, a column setting step that sets a number of columns equal to the number of items set in the item setting step;

a matrix generating step that generates a matrix composed of a number of rows given by adding one to the number of rows set in the row setting step and a number of columns given by adding one to the number of columns set in the column setting step;

a first column inserting step that inserts the types of DNA chips into respective cells in a first column of the matrix;

a first row inserting step that inserts the items into respective cells in a first row of the matrix;

a cell inserting step that inserts, into respective cells at intersections of columns and rows in the matrix, experiment data for a combination of a type of DNA chip in the row to which the cell belongs and an item in the column to which the cell belongs; and a matrix drawing step that draws a matrix composed of cells in which the types of DNA chip, the items, and the experiment data have been inserted.

\* \* \* \* \*